(12) United States Patent
Griesbach, III

(10) Patent No.: US 7,178,171 B2
(45) Date of Patent: Feb. 20, 2007

(54) ELASTOMERIC GLOVES HAVING ENHANCED BREATHABILITY

(75) Inventor: Henry L. Griesbach, III, Clarkston, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 631 days.

(21) Appl. No.: 10/223,592

(22) Filed: Aug. 19, 2002

(65) Prior Publication Data
US 2004/0031087 A1   Feb. 19, 2004

(51) Int. Cl.
A41D 19/00   (2006.01)

(52) U.S. Cl. .......................................... 2/161.7
(58) Field of Classification Search ............. 2/161.7, 2/161.6, 160, 167; 428/98; 442/181, 327
See application file for complete search history.

(56) References Cited

U.S. PATENT DOCUMENTS

| | | | |
|---|---|---|---|
| 1,519,913 A | 12/1924 | Hynes | |
| 3,338,992 A | 8/1967 | Kinney | |
| 3,341,394 A | 9/1967 | Kinney | |
| 3,485,787 A | 12/1969 | Haefele et al. | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,813,695 A * | 6/1974 | Podell et al. | 2/168 |
| 3,830,767 A | 8/1974 | Condon | |
| 4,006,116 A | 2/1977 | Dominguez | |
| 4,039,629 A | 8/1977 | Himes et al. | |
| 4,041,103 A | 8/1977 | Davison et al. | |
| 4,304,008 A | 12/1981 | Joung | |
| 4,340,563 A | 7/1982 | Appel et al. | |
| 4,373,519 A | 2/1983 | Errede et al. | |
| 4,386,179 A | 5/1983 | Sterling | |
| 4,394,473 A | 7/1983 | Winter et al. | |
| 4,430,759 A | 2/1984 | Jackrel | |

(Continued)

FOREIGN PATENT DOCUMENTS

EP   0815880 A2   1/1998

(Continued)

OTHER PUBLICATIONS

Abstract of Japanese Patent No. 08176910, Dec. 26, 1994.

(Continued)

*Primary Examiner*—Katherine M. Moran
(74) *Attorney, Agent, or Firm*—Dority & Manning, P.A.

(57) ABSTRACT

An elastomeric glove that contains zones of differing water vapor transmission rates is provided. The glove contains at least one liquid and vapor impermeable zone, i.e., "moisture-impermeable" zone. Such moisture-impermeable zones generally have a WVTR of less than about 1500 $g/m^2/24$ hours. Further, the glove also contains at least one liquid-impermeable, but vapor-permeable zone, i.e., "breathable" zone. Such breathable zones generally have a WVTR of at least about 250 $g/m^2/24$ hours. As a result, the glove may sufficiently inhibit liquids and moisture from contacting the hand during use, and allow water vapor that would otherwise accumulate on the skin of a user to escape from the glove, thereby enhancing the comfort of the user's hands during long periods of use.

35 Claims, 1 Drawing Sheet

U.S. PATENT DOCUMENTS

| | | |
|---|---|---|
| 4,434,126 A | 2/1984 | McGary, Jr. et al. |
| 4,463,156 A | 7/1984 | McGary, Jr. et al. |
| 4,481,323 A | 11/1984 | Sterling |
| 4,499,154 A | 2/1985 | James et al. |
| 4,511,354 A | 4/1985 | Sterling |
| 4,514,460 A | 4/1985 | Johnson |
| 4,520,056 A | 5/1985 | Jackrel |
| 4,548,844 A | 10/1985 | Podell et al. |
| 4,555,813 A | 12/1985 | Johnson |
| 4,576,156 A | 3/1986 | Dyck et al. |
| 4,613,640 A | 9/1986 | Deisler et al. |
| 4,660,228 A | 4/1987 | Ogawa et al. |
| 4,670,330 A | 6/1987 | Ishiwata |
| 4,684,490 A | 8/1987 | Taller et al. |
| 4,725,481 A | 2/1988 | Ostapchenko |
| 4,777,073 A | 10/1988 | Sheth |
| 4,783,857 A | 11/1988 | Suzuki et al. |
| 4,789,720 A | 12/1988 | Teffenhart |
| 4,810,543 A | 3/1989 | Gould et al. |
| 4,818,600 A | 4/1989 | Braun et al. |
| 4,888,829 A | 12/1989 | Kleinerman et al. |
| 4,917,850 A | 4/1990 | Gray |
| 4,920,172 A | 4/1990 | Daoud |
| 4,968,741 A | 11/1990 | Burroway et al. |
| 5,011,409 A | 4/1991 | Gray |
| 5,014,361 A | 5/1991 | Gray |
| 5,014,362 A | 5/1991 | Tillotson et al. |
| 5,020,161 A | 6/1991 | Lewis, Jr. et al. |
| 5,020,162 A | 6/1991 | Kersten et al. |
| 5,026,591 A | 6/1991 | Henn et al. |
| 5,026,607 A | 6/1991 | Kiezulas |
| 5,088,125 A | 2/1992 | Ansell et al. |
| 5,112,900 A | 5/1992 | Buddenhagen et al. |
| 5,120,816 A | 6/1992 | Gould et al. |
| 5,123,119 A | 6/1992 | Dube |
| 5,132,129 A | 7/1992 | Potter et al. |
| 5,146,628 A | 9/1992 | Herrmann et al. |
| 5,187,815 A | 2/1993 | Stern et al. |
| 5,195,537 A | 3/1993 | Tillotson |
| 5,244,716 A | 9/1993 | Thornton et al. |
| 5,272,012 A | 12/1993 | Opolski |
| 5,272,771 A | 12/1993 | Ansell et al. |
| 5,302,440 A | 4/1994 | Davis |
| 5,310,517 A | 5/1994 | Dams et al. |
| 5,343,586 A | 9/1994 | Vosbikian |
| 5,370,900 A | 12/1994 | Chen |
| 5,382,400 A | 1/1995 | Pike et al. |
| 5,391,343 A | 2/1995 | Dreibelbis et al. |
| 5,395,666 A | 3/1995 | Brindle |
| 5,405,666 A | 4/1995 | Brindle |
| 5,407,715 A | 4/1995 | Buddenhagen et al. |
| 5,458,936 A | 10/1995 | Miller et al. |
| 5,483,703 A | 1/1996 | Williams |
| 5,520,980 A | 5/1996 | Morgan et al. |
| 5,534,350 A | 7/1996 | Liou |
| 5,545,451 A | 8/1996 | Haung et al. |
| 5,554,673 A | 9/1996 | Shah |
| 5,570,475 A | 11/1996 | Nile et al. |
| 5,571,567 A | 11/1996 | Shah |
| 5,576,382 A | 11/1996 | Seneker et al. |
| 5,601,870 A | 2/1997 | Haung et al. |
| 5,612,083 A | 3/1997 | Haung et al. |
| 5,620,773 A | 4/1997 | Nash |
| 5,636,382 A * | 6/1997 | Chopko et al. ............... 2/167 |
| 5,644,798 A | 7/1997 | Shah |
| 5,649,326 A | 7/1997 | Richard, Jr. et al. |
| 5,650,225 A | 7/1997 | Dutta et al. |
| 5,660,918 A | 8/1997 | Dutta |
| RE35,616 E | 9/1997 | Tillotson et al. |
| 5,682,613 A | 11/1997 | Dinatale |
| 5,695,868 A | 12/1997 | McCormack |
| 5,728,340 A | 3/1998 | Dreibelbis et al. |
| 5,736,251 A | 4/1998 | Pinchuk |
| 5,740,551 A | 4/1998 | Walker |
| 5,742,943 A | 4/1998 | Chen |
| 5,792,531 A | 8/1998 | Littleton et al. |
| 5,832,539 A | 11/1998 | Williams |
| 5,833,915 A | 11/1998 | Shah |
| 5,843,057 A | 12/1998 | McCormack |
| 5,846,604 A * | 12/1998 | Caldwell ................... 427/245 |
| 5,855,999 A | 1/1999 | McCormack |
| 5,881,386 A | 3/1999 | Horwege et al. |
| 5,884,639 A | 3/1999 | Chen |
| 5,900,452 A | 5/1999 | Plamthottam |
| 5,906,823 A | 5/1999 | Mixon |
| 5,948,707 A | 9/1999 | Crawley et al. |
| 5,962,620 A | 10/1999 | Reich et al. |
| 5,977,223 A | 11/1999 | Ryan et al. |
| 5,985,392 A | 11/1999 | Hert et al. |
| 5,985,955 A | 11/1999 | Bechara et al. |
| 5,993,972 A | 11/1999 | Reich et al. |
| 5,997,969 A | 12/1999 | Gardon |
| 5,998,540 A | 12/1999 | Lipkin et al. |
| 6,002,064 A | 12/1999 | Kobylivker et al. |
| 6,015,764 A | 1/2000 | McCormack et al. |
| 6,017,997 A | 1/2000 | Snow et al. |
| 6,019,922 A | 2/2000 | Hassan et al. |
| 6,021,524 A | 2/2000 | Wu et al. |
| 6,037,281 A | 3/2000 | Mathis et al. |
| 6,045,900 A | 4/2000 | Haffner et al. |
| 6,048,932 A | 4/2000 | Okada et al. |
| 6,051,320 A | 4/2000 | Noecker et al. |
| 6,075,179 A | 6/2000 | McCormack et al. |
| 6,143,416 A | 11/2000 | Brindle et al. |
| 6,154,886 A | 12/2000 | Hottner |
| 6,172,177 B1 | 1/2001 | Wang et al. |
| 6,261,674 B1 | 7/2001 | Branham et al. |
| 6,277,479 B1 * | 8/2001 | Campbell et al. ........... 428/213 |
| 6,288,159 B1 | 9/2001 | Plamthottam |
| 6,306,514 B1 | 10/2001 | Weikel et al. |
| 6,347,408 B1 | 2/2002 | Yeh |
| 6,348,258 B1 | 2/2002 | Topolkaraev et al. |
| 6,389,602 B1 | 5/2002 | Alsaffar |
| 6,647,549 B2 * | 11/2003 | McDevitt et al. ................ 2/21 |
| 2002/0119300 A1 | 8/2002 | Taylor |

FOREIGN PATENT DOCUMENTS

| | | |
|---|---|---|
| EP | 0815880 A3 | 1/1998 |
| EP | 0760834 | 10/1998 |
| EP | 0931633 A2 | 7/1999 |
| EP | 1264684 A1 | 12/2002 |
| JP | 08158124 | 6/1996 |
| WO | WO 9628221 | 9/1996 |
| WO | WO 9716082 | 5/1997 |
| WO | WO 9810669 A1 | 3/1998 |
| WO | WO 9858796 | 12/1998 |
| WO | WO 9907548 | 2/1999 |
| WO | WO 9912734 A1 | 3/1999 |
| WO | WO 9964240 | 12/1999 |

OTHER PUBLICATIONS

PCT Search Report, Nov. 11, 2003.

* cited by examiner

ELASTOMERIC GLOVES HAVING ENHANCED BREATHABILITY

BACKGROUND OF THE INVENTION

Elastomeric gloves, such as surgical and examination gloves, are routinely made from natural and/or synthetic elastomers to achieve a combination of good elasticity and strength. During use, it is generally desired that the gloves remain relatively impermeable to liquids to protect the hands of the user. For instance, liquid-impermeable gloves may protect the medical staff from blood and other liquids often encountered during surgery and other medical procedures. Unfortunately, the same characteristic of the glove that protects the hands of the user, i.e., liquid-impermeability, can also cause multiple problems. In particular, water vapor may accumulate on the surface of the skin under the glove after a certain period of time. This accumulation may cause irritation, rashes, itchiness, and the like, particularly when the gloves are worn for a long period of time.

As such, a need currently exists for an elastomeric glove that provides the desired liquid-impermeability, but also alleviates the accumulation of water vapor during periods of use.

SUMMARY OF THE INVENTION

In accordance with one embodiment of the present invention, an elastomeric glove is disclosed that comprises a substrate body. The substrate body defines at least one breathable zone and at least one moisture-impermeable zone. The moisture-impermeable zone includes an elastomeric material. The substrate body may form a palm side, a top hand side, and fingers regions. In such an instance, the breathable zone may, in some embodiments, constitute at least a portion of the top hand side, while the moisture-impermeable zone may constitute at least a portion of the finger regions, the palm side, or combinations thereof.

The breathable zone has a water vapor transmission rate that is at least about 15% greater than the water vapor transmission rate of the moisture-impermeable zone. In some embodiments, the breathable zone has a water vapor transmission rate that is at least about 50% greater than the water vapor transmission rate of the moisture-impermeable zone. Further, in some embodiments, the breathable zone has a water vapor transmission rate that is at least about 100% greater than the water vapor transmission rate of the moisture-impermeable zone. For example, the breathable zone may have a moisture vapor transmission rate greater than about 250 grams per square meter per 24 hours. In some embodiments, the breathable zone may have a moisture vapor transmission rate greater than about 1000 grams per square meter per 24 hours. Further, in some embodiments, the breathable zone may have a moisture vapor transmission rate greater than about 3000 grams per square meter per 24 hours. In some embodiments, the breathable zone may have a moisture vapor transmission rate greater than about 5000 grams per square meter per 24 hours. Likewise, the moisture-impermeable zone may have a water vapor transmission rate that is less than about 500 grams per square meter per 24 hours. Further, in some embodiments, the moisture-impermeable zone may have a water vapor transmission rate that is less than about 250 grams per square meter per 24 hours.

The differential water vapor transmission rates desired in the present invention can be provided in a variety of different ways. For example, in some embodiments, the breathable zone contains at least one material that is different than the material forming the moisture-impermeable zone. The breathable zone may, for instance, contain a breathable film. In other embodiments, the breathable zone may be formed from the same material as the moisture-impermeable zone. In one such embodiment, the breathable zone and the moisture-impermeable zone include polyurethane. In some embodiments, such as where the moisture-impermeable and breathable zones are formed from the same material, the thickness of the breathable zone is at least about 25% less than the thickness of the moisture-impermeable zone. Further, in some embodiments, the thickness of the breathable zone is from about 50% to about 95% less than the thickness of the moisture-impermeable zone.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
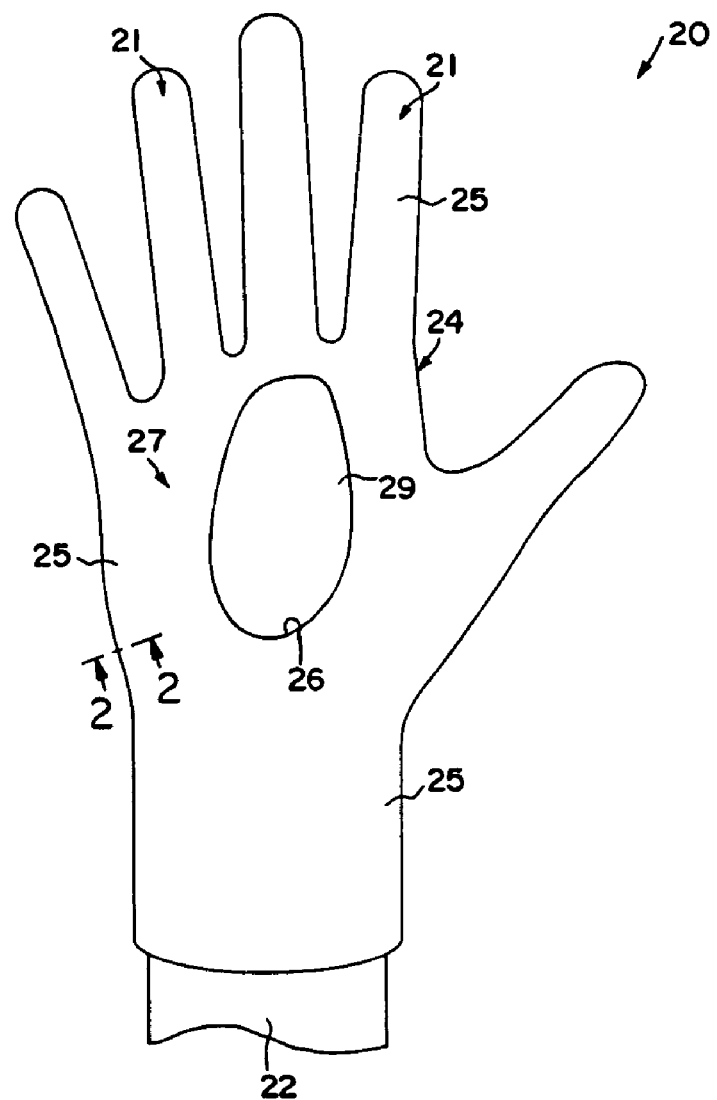
FIG. 1 is a perspective view of one embodiment of an elastomeric glove made according to the invention.

Repeat use of reference characters in the present specification and drawings is intended to represent the same or analogous features or elements of the invention.

DETAILED DESCRIPTION OF REPRESENTATIVE EMBODIMENTS

DEFINITIONS

As used herein, the "water vapor transmission rate" (WVTR) generally refers to the rate at which water vapor permeates through a material as measured in units of grams per meter squared per 24 hours ($g/m^2/24$ hrs). The test used to determine the WVTR of a material may vary based on the nature of the material. For instance, in some embodiments, WVTR may be determined in general accordance with ASTM Standard E-96E-80. This test may be particularly well suited for materials thought to have a WVTR of up to about 3,000 $g/m^2$124 hrs. Another technique for measuring WVTR involves the use of a PERMATRAN-W 100K water vapor permeation analysis system, which is commercially available from Modern Controls, Inc. of Minneapolis, Minn. Such a system may be particularly well suited for materials thought to have a WVTR of greater than about 3,000 $g/m^2/24$ hrs. However, as is well known in the art, it should also be understood that other systems and techniques for measuring WVTR may also be utilized in the present invention.

As used herein, the term "moisture impermeable" refers to a material that does not readily allow a liquid, such as water, to pass therethrough. The "moisture impermeability" of a material may be measured in terms of water vapor transmission rate (WVTR), with higher values representing a less moisture-impermeable material and lower values representing a more moisture-impermeable material. In some embodiments, moisture-impermeable materials have a WVTR of less than about 1500 grams per square meter per 24 hours ($g/m^2/24$ hours). The WVTR may be less than about 1000 $g/m^2/24$ hours. Further, the WVTR may less than about 500 g/m²/24 hours. In some embodiments, the WVTR may be less than about 250 g/m²/24 hours.

As used herein, the term "breathable" means pervious to water vapor and gases, but impermeable to liquid water. For instance, "breathable barriers" and "breathable films" allow water vapor to pass therethrough, but are substantially impervious to liquid water. The "breathability" of a material is measured in terms of water vapor transmission rate (WVTR), with higher values representing a more breathable material and lower values representing a less breathable material. Breathable materials generally have a WVTR of greater than about 250 grams per square meter per 24 hours (g/m²/24 hours). In some embodiments, the WVTR may be greater than about 1000 g/m²124 hours. Further, in some embodiments, the WVTR may be greater than about 3000 g/m²/24 hours. In some embodiments, the WVTR may be greater than about 5000 g/m²/24 hours.

As used herein the term "nonwoven fabric" or "nonwoven web" means a web having a structure of individual fibers or threads which are interlaid, but not in an identifiable manner as in a knitted fabric. Some examples of nonwoven fabrics or webs include, but are not limited to, meltblown webs, spunbonded webs, airlaid webs, bonded carded webs, etc.

As used herein, the term "meltblown web" refers to a nonwoven web formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonded web" refers to a nonwoven web containing small diameter substantially continuous fibers that are formed by extruding a molten thermoplastic material as filaments from a plurality of fine, usually circular, capillaries of a spinnerette with the diameter of the extruded fibers then being rapidly reduced as by, for example, eductive drawing and/or other well-known spunbonding mechanisms. The production of spunbonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to an elastomeric glove that contains zones of differing water vapor transmission rates. For example, the glove of the present invention contains at least one liquid and vapor impermeable zone, i.e., "moisture-impermeable" zone and at least one liquid-impermeable, but vapor-permeable zone, i.e., "breathable" zone. Generally speaking, at least one of the breathable zones has a WVTR at least about 15% greater than the WVTR of a moisture-impermeable zone. In some embodiments, at least one of the breathable zones has a WVTR at least about 50% greater than the WVTR of a moisture-impermeable zone. Further, in some embodiments, at least one of the breathable zones has a WVTR at least about 100% greater than the WVTR of a moisture-impermeable zone. By containing one or more moisture-impermeable zones, the glove of the present invention may sufficiently inhibit liquids and moisture exterior to the glove from contacting the hand during use. This impermeability may facilitate use of the glove in a multitude of applications, such as in medical, surgical, and clean room environments. Further, the use of one or more breathable zones allows skin-derived water vapor that would otherwise accumulate next to the skin of a user to transpire from the glove, thereby enhancing the comfort of the user's hands during long periods of use.

Figure 2:
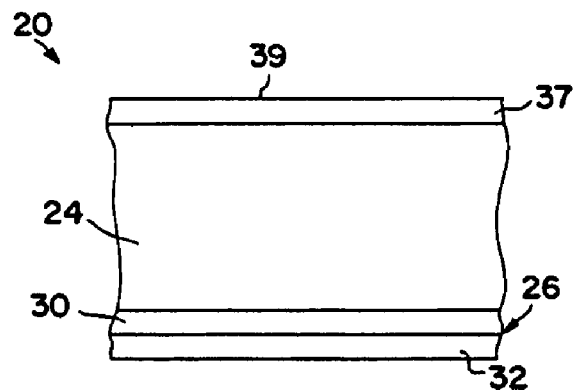
FIG. 2 is a cross-sectional view of the glove illustrated in FIG. 1 taken along a line 2—2.

Referring to FIGS. 1–2, for example, one embodiment of an elastomeric glove 20 is illustrated that may be placed on the hand of a user 22. The glove 20 includes a substrate body 24 having finger regions 21 and a palm side (not shown) that define moisture-impermeable zones 25. Further, the substrate body 24 also has a top hand side 27 that defines one or more moisture-permeable, but liquid-impermeable zones, i.e., "breathable" zones 29. It should be understood, however, that the glove 20 may generally contain any number of moisture impermeable zones 25 and breathable zones 29. Further, it should also be understood that the zones 25 and 29 may be located at any location of the glove 20.

The size and shape of the moisture-impermeable and breathable zones 25 and 29 may generally vary as desired. The breathable zones 29 may constitute a substantial portion of the glove 20 or may constitute only a small portion of the glove 20, so long as the glove contains at least one breathable zone 29 of a predetermined area. For example, in some embodiments, the total area of the breathable zones 29 is from about 1 to about 15 square inches (in²). Further, in some embodiments, the total area of the breathable zones 29 is from about 2 to about 10 in². As mentioned, the shape of the breathable zones 29 may also vary. Some suitable shapes for the breathable zones 29 include circles, squares, rectangles, ovals, triangles, and various other regular or irregular shapes. When utilizing multiple breathable zones 29, it should also be understood that the zones 29 may be continuous and/or discontinuous. For example, in one embodiment, the breathable zones 29 may constitute multiple portions positioned across the top hand side 27 of the glove 20 in a discontinuous manner.

Generally speaking, the moisture-impermeable zone(s) 25 of the glove may be formed from any of a variety of natural and/or synthetic elastomeric materials known in the art. For instance, some examples of suitable elastomeric materials include, but are not limited to, S-EB-S (styrene-ethylene-butylene-styrene) block copolymers, S-I-S (styrene-isoprene-styrene) block copolymers, S-B-S (styrene-butadiene-styrene) block copolymers, S-I (styrene-isoprene) block copolymers, S-B (styrene-butadiene) block copolymers, natural rubber latex, nitrile rubbers (e.g., acrylonitrile butadiene), isoprene rubbers, chloroprene rubbers, polyvinyl chlorides, silicone rubbers, polyurethane, and combinations thereof. Other suitable elastomeric materials that may be used to form the moisture-impermeable zone(s) may be described in U.S. Pat. No. 6,306,514 to Weikel, et al., which is incorporated herein in its entirety by reference thereto for all purposes.

In one embodiment, for example, one or more elastomeric block copolymers are utilized. S-EB-S block copolymers and methods for forming solutions thereof are described in U.S. Pat. No. 5,112,900 to Buddenhagen, et al.; U.S. Pat. No. 5,407,715 to Buddenhagen, et al.; U.S. Pat. No. 5,900,452 to Plamthottam; and U.S. Pat. No. 6,288,159 to Plamthottam, which are incorporated herein in their entirety by reference thereto for all purposes. Some commercially available examples of S-EB-S block copolymers include, but are not limited to, Kraton® G1650, Kraton® G1651, and Kraton® G1652, which are available from Kraton Polymers of Houston, Tex. Kraton® G1650 is an S-EB-S block copolymer having a styrene/central block ratio of 28/72 and a Brookfield Viscosity in toluene solution (20% concentration by weight) at 77° F. of 1500 centipoise. Kraton® G1651 is an S-EB-S block copolymer having a styrene/central block ratio of 33/67 and a Brookfield Viscosity in toluene solution (20% concentration by weight) at 77° F. of 2000 centipoise. Kraton® G1652 is an S-EB-S block copolymer having a styrene/central block ratio of 29/71 and a Brookfield Viscosity in toluene solution (20% concentration by weight) at 77° F. of 550 centipoise.

The breathable zone(s) 29 of the elastomeric glove 20 may be formed from the same or a different material than the moisture-impermeable zone 25. For example, in one embodiment, the breathable zone 29 contains at least one material that is not included within the moisture-impermeable zone 25. The breathable zone 29 may overlap the moisture-impermeable zone 25 and be hermetically sealed thereto. As a result, the entire glove may remain generally impermeable to liquids. To hermetically seal the breathable zone 29 to the moisture-impermeable zone 25, a variety of well-known techniques may be utilized. For instance, the breathable zone 29 may be sealed to the moisture-impermeable zone 25 using adhesives, thermal bonding, sonic bonding, dip coating, partial coating, and the like. As shown in FIGS. 1–2, for instance, the breathable zone 29 is sealed to the moisture impermeable zone 25 at bonding locations 26.

When formed from a different material than the moisture-impermeable zone 25, the breathable zone 29 may generally contain any material capable of achieving the desired moisture permeability and liquid impermeability. For instance, the breathable zone 29 may be formed from films, nonwoven webs, nonwovens coated with a film-forming material (e.g., an emulsion coated onto a meltblown web or a laminate comprising spunbond and meltblown webs), combinations thereof, and the like. For example, a film may be constructed with micropores therein to provide breathability. The micropores form what is often referred to as tortuous pathways through the film. Liquid contacting one side of the film does not have a direct passage through the film. Instead, a network of microporous channels in the film prevents liquids from passing, but allows gases and water vapor to pass. Another type of film that may be used is a nonporous, continuous film, which, because of its molecular structure and thickness, is capable of forming a vapor-pervious barrier. Among the various polymeric films that fall into this type include films made from a sufficient amount of poly (vinyl alcohol), polyvinyl acetate, ethylene vinyl alcohol, polyurethane, ethylene methyl acrylate, ethylene methyl acrylic acid, and other films that contain hydrophilic components to make them breathable. Without intending to be held to a particular mechanism of operation, it is believed that films made from such polymers have sufficient levels of water solubility to allow transportation of those molecules from one surface of the film to the other. Accordingly, these films may be sufficiently continuous, i.e., nonporous, to make them liquid-impermeable, but still allow for vapor permeability. These films may be single- or multi-layered, and may be formed by extrusion, solvent casting, and other known techniques. The post-formed may also be stretched to achieve the desired thickness dimension.

In some embodiments, the breathable zone 29 may be made from polymer films that contain a filler, such as calcium carbonate. As used herein, a "filler" generally refers to particulates and other forms of materials that may be added to the film polymer extrusion blend and that will not chemically interfere with the extruded film, but which may be uniformly dispersed throughout the film. Generally, the fillers are in particulate form and have a spherical or non-spherical shape with average particle sizes in the range of from about 0.1 to about 7 microns. Both organic and inorganic fillers are contemplated to be within the scope of the present invention. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as, for example, stearic acid, may also be applied to the filler particles if desired.

These films are made breathable by stretching the filled films to create the microporous passageways as the polymer breaks away from the calcium carbonate during stretching. For example, in one embodiment, the breathable zone 29 contains a stretch-thinned film that includes at least two basic components, i.e., a polyolefin polymer and a filler. These components are mixed together, heated, and then extruded into a film layer using any of a variety of film-producing processes known to those of ordinary skill in the film processing art. Such film-making processes include, for example, cast embossed, chill and flat cast, and blown film processes.

Generally, on a dry weight basis, based on the total weight of the film, the stretch-thinned film includes from about 30% to about 90% by weight of a polyolefin polymer. In some embodiments, the stretch-thinned film includes from about 30% to about 90% by weight of a filler. Examples of such films are described in U.S. Pat. No. 5,843,057 to McCormack; U.S. Pat. No. 5,855,999 to McCormack; U.S. Pat. No. 6,002,064 to Kobylivker, et al.; and U.S. Pat. No. 6,037,281 to Mathis, et al., which are incorporated herein in their entirety by reference thereto for all purposes. In one embodiment, the polyolefin polymer may be a predominately linear polyolefin polymer, such as linear, low-density polyethylene (LLDPE) or polypropylene. The term "linear low density polyethylene" refers to polymers of ethylene and higher alpha olefin comonomers, such as $C_3$–$C_{12}$ and combinations thereof, having a Melt Index (as measured by ASTM D-1238) of from about 0.5 to about 10 grams per 10 minutes at 190° C. Moreover, the term "predominately linear" means that the main polymer chain is linear with less than about 5 long chain branches per 1000 ethylene units. Long chain branches include, for example, carbon chains greater than $C_{12}$. For predominately linear polyolefin polymers that are nonelastic, short chain branching ($C_3$–$C_{12}$) due to comonomer inclusion is typically less than about 20 short chains per 1000 ethylene units and about 20 or greater for polymers that are elastomeric. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers.

As mentioned herein, the stretch-thinned film may be formed using any conventional process known to those familiar with film formation. For example, the polyolefin polymer and filler are first mixed in the desired proportions, blended with the application of heat, and then extruded into a film. To provide more uniform breathability, as reflected by the water vapor transmission rate of the film, the filler may be uniformly dispersed throughout the extruded blend and, consequently, throughout the film itself. The film is uniaxially or biaxially stretched. The film may be uniaxially stretched, for example, to about 1.1 to about 7.0 times its original length. In some embodiments, the film may be stretched to about 1.5 to about 6.0 times its original length. Further, in some embodiments, the film may be stretched to about 2.5 to about 5.0 times its original length. The film may alternatively be biaxially stretched using techniques familiar to one of ordinary skill in the art.

Breathable films, such as described above, may constitute an entire breathable zone 29, or may be part of a multilayer film. Multilayer films may be prepared by cast or blown film coextrusion of the layers, by extrusion coating, or by any conventional layering process. Breathable, multilayer films may contain fillers in one or more of the layers. One example of a multilayer film containing a filler in each layer is described in U.S. Pat. No. 6,045,900 to Haffner, et al., which is incorporated herein in its entirety by reference thereto for all purposes. Likewise, one example of a multilayer film that contains a reduced level of filler, or no filler, within the layers is described in U.S. Pat. No. 6,075,179 to McCormack, et al., which is incorporated herein in its entirety by reference thereto for all purposes. If desired, the breathable film may also be bonded to a nonwoven fabric, knitted fabric, and/or woven fabric using well-known techniques. For instance, suitable techniques for bonding a film to a nonwoven web are described in U.S. Pat. No. 5,843,057 to McCormack; U.S. Pat. No. 5,855,999 to McCormack; U.S. Pat. No. 6,002,064 to Kobylivker, et al.; U.S. Pat. No. 6,037,281 to Mathis, et al.; and WO 99/12734, which are incorporated herein in their entirety by reference thereto for all purposes. In one embodiment, for example, a breathable, liquid-impermeable, breathable film/nonwoven laminate material may be formed from a nonwoven layer and a breathable film layer. The layers may be arranged so that the breathable film layer is attached to the nonwoven layer.

In addition, besides being formed from a material that is different than the moisture-impermeable zone 25, the breathable zone 29 may also be formed from the same material as the moisture-impermeable zone 25. In such embodiments, the breathable zone 29 may be formed separately and/or in conjunction with the moisture-impermeable zone 25. To achieve the desired moisture permeability differentiation between the zones 25 and 29, the thickness of each zone may be varied. Thus, for example, the thickness of the breathable zone 29 may be at least about 25% less than the thickness of the moisture-impermeable zone 25. Further, in some embodiments, the thickness of the breathable zone 29 may be at least about 50% less than the thickness of the moisture-impermeable zone 25. In some embodiments, the thickness of the breathable zone 29 may be from about 50% to about 95% less than the thickness of the moisture-impermeable zone 25. When the breathable zone 29 is reinforced with a strengthening material, such as a nonwoven web, the thickness of the breathable zone 29 may be even smaller.

For illustrative purposes, several examples of thickness ranges that may be used for a glove of the present invention will now be described in more detail. For instance, the thickness of the moisture-impermeable zone 25 may range from about 0.01 millimeters to about 0.50 millimeters. In some embodiments, the thickness of the moisture-impermeable zone 25 may range from about 0.06 millimeters to about 0.35 millimeters. The thickness of the breathable zone 29 may be less than, the same, or greater than the thickness of the moisture-impermeable zone 25. For instance, in some embodiments, the thickness of the breathable zone 29 may range from about 0.001 millimeters to about 1.5 millimeters. When the breathable zone 29 is formed from the same material as the moisture-impermeable zone 25, for example, its thickness may range from about 0.01 to about 0.03 millimeters. In some instances, when the breathable zone 29 is a combination of a breathable film and a reinforcing material (e.g., scrim or nonwoven web), its thickness may range from about 0.003 millimeters to about 0.35 millimeters. It should be understood, however, that the thickness of the breathable zone 29 may also be the same or greater than the thickness of the moisture-impermeable zone 25, particularly when the breathable zone 29 and the moisture-impermeable zone 25 are formed from a different material, such as when the breathable zone 29 is a combination of a film and reinforcing material.

When formed from the same material, it is typically desired that the breathable zone 29 and moisture-impermeable zone 25 contain an elastomeric material to enable the glove 20 to readily conform to the shape of a user's hand. One example of a suitable elastomeric material that is believed to be capable of imparting the desired moisture permeability differentiation between the zones 25 and 29 when provided at different thicknesses is polyurethane, such as film-forming thermoplastic polyurethanes (e.g., both aliphatic-polyether and aliphatic-polyester types) and polyether amides (e.g., Pebax®, which is available from Atochem North America, Inc. of Philadelphia, Pa.). Various types of polyurethane that may be suitable for this purpose are described in more detail in U.S. Pat. No. 4,888,829 to Kleinerman, et al. and U.S. Pat. No. 5,650,225 to Dutta, et al., which are incorporated herein in their entirety by reference thereto for all purposes.

Referring again to FIGS. 1–2, the glove 20 may also contain additional layers. For example, as shown in FIG. 2, the glove 20 may contain a coating 26 that contacts the body of the user 22 during use. In this embodiment, the coating 26 includes a donning layer 30 overlying and contacting at least a portion of the substrate body 24 and a lubricant 32 overlying and contacting at least a portion of the donning layer 30. It should be understood that, when using a donning layer 30 or lubricant 32 that is moisture-impermeable, it may be desired that such layers be arranged on the glove 20 so that the breathable zones 29 remain free to allow the removal of water vapor from the glove 20 during use. For example, the donning layer 30 and/or lubricant 32 may be coated only on the inside surface of the moisture-impermeable zone 29 of the glove 20.

The donning layer 30 may contain any of a variety of different elastomeric polymers that are capable of facilitating donning of the glove. Some examples of suitable materials for the donning layer 30 include, but are not limited to, polybutadienes (e.g., syndiotactic 1,2 polybutadiene), polyurethanes, halogenated copolymers, and the like. For instance, in one embodiment, an unsaturated styrene-isoprene (SIS) having tri- or radial-blocks may be utilized. In some embodiments, the SIS block copolymer has a polystyrene end block content of from about 10% to about 20% by weight of the total weight of the SIS block copolymer. In another embodiment, the SIS block copolymer has a polystyrene end block content of from about 15% to about 18% by weight, of the total weight of the SIS block copolymer. Moreover, the molecular weight of the polystyrene end blocks is typically at least about 5,000 grams per mole. Some examples of suitable mid-block unsaturated SIS block copolymers include, but are not limited to, Kraton® D 1107 available from Kraton Polymers and Vector® 511 and Vector® 4111 available from Dexco Polymers of Houston, Tex.

Another suitable donning material is 1,2 polybutadiene (e.g., syndiotactic 1,2 polybutadiene). In one embodiment, for example, the donning layer 30 is formed from a solution that contains 5.0 weight % Presto Emulsion (15% solids), 2.0 weight % magnesium carbonate, 3.0 weight % compounded natural rubber latex, and 90.0 weight % deionized water. The "Presto Emulsion" is manufactured by Ortec, Inc. of Easley, S.C. and is an emulsion of 1,2 syndiotactic polybutadiene in water. Other examples of donning materials that may be utilized in the donning layer 30 may be described in U.S. Pat. No. 5,792,531 to Littleton, et al., which is incorporated herein in its entirety by reference thereto for all purposes.

A lubricant 32 may also coat the donning layer 30 to aid in donning the article when the user's body is either wet or dry. The lubricant 32, for example, may include a cationic surfactant (e.g., cetyl pyridinium chloride), an anionic surfactant (e.g., sodium lauryl sulfate), a nonionic surfactant, and the like. For instance, in one embodiment, the lubricant 32 contains a quaternary ammonium compound, such as that available Goldschmidt Chemical Corp. of Dublin, Ohio under the trade name Verisoft BTMS, and a silicone emulsion, such as that obtained from General Electric Silicone under the trade name AF-60. Verisoft BTMS contains behnyl trimethyl sulfate and cetyl alcohol, while AF-60 contains polydimethylsiloxane, acetylaldehyde, and small percentages of emulsifiers. In another embodiment, the lubricant 32 contains a silicone emulsion, such as DC 365 (Dow Corning) or SM 2140 (GE Silicones).

Further, besides the above-mentioned layers, the glove 20 may also contain additional layers if desired. For example, in one embodiment, the glove 20 contains a layer 37 that defines an environment-exposed surface 39 of the glove 20. Although optional, the layer 37 may, for example, be utilized to facilitate gripping on the outer surface 39. For example, in one embodiment, the layer 37 may contain a silicone emulsion, such as DC 365 (Dow Corning) or SM 2140 (GE Silicones). It should also be understood, however, that the substrate body 24 may define the environment-exposed surface 39 of the glove 20.

An elastomeric glove made in accordance with the present invention may generally be formed using a variety of processes known in the art. In fact, any process capable of making an elastomeric glove may be utilized in the present invention. For example, elastomeric glove formation techniques may utilize dipping, spraying, chlorination, drying, curing, as well as any other technique known in the art. Some examples of suitable methods for forming a glove that may be used in the present invention are described in U.S. Pat. No. 5,112,900 to Buddenhagen, et al.; U.S. Pat. No. 5,407,715 to Buddenhagen, et al.; U.S. Pat. No. 5,742,943 to Chen; U.S. Pat. No. 5,792,531 to Littleton, et al.; U.S. Pat. No. 5,900,452 to Plamthottam; U.S. Pat. No. 6,288,159 to Plamthottam; and U.S. Pat. No. 6,306,514 to Weikel, et al., which are incorporated herein in their entirety by reference thereto for all purposes.

In one embodiment, for example, a glove-shaped former, such as made from metals, ceramics, or plastics, is utilized to form the glove body. As is well known in the art, such formers can be dipped into one more tanks containing a bath of polymer latex (e.g., natural rubber latex, nitrile, polyurethane, etc.). Thereafter, the polymer latex may be cured to form the glove body. Other layers, such as a donning layer or lubricant, may be formed on the glove body using techniques well known in the art.

Generally, a variety of different techniques may be used to impart the glove with the desired moisture-impermeable and breathable zones. For instance, in some embodiments, the breathable material may be applied onto at least a portion of the former (e.g., top of the hand portion of the former) before it is dipped into the polymer latex bath. Accordingly, the resulting latex body may partially overlap the breathable material to form moisture-impermeable and breathable zones. Upon being cured, the breathable zones will be hermetically sealed to the moisture-impermeable zones.

In other embodiments, the former may be dipped into one or more baths of polymer latex in such a manner that portions of the glove have an intentionally different thickness. This may be accomplished using techniques well known in the art. For example, in one embodiment, a first portion of the former (e.g., fingers and palm side of the former) may be dipped into a first polymer latex bath for a certain period of time. Upon being removed from the first bath, a second portion of the former (e.g., top hand side of the former) may be dipped into a second polymer latex that is the same or different than the first polymer latex. To provide a differential thickness across the glove, the dipping conditions (e.g., dipping time, solid content of bath, etc.) may be varied for each dipping step. For instance, the former may be dipped into the first latex bath for a time period that is longer than the time period in which the former is dipped into the second latex bath. This allows the first portion of the former to be thicker than the second portion of the former, which as discussed above, may result in the desired difference in breathability for the glove.

Although various constructions and techniques for forming elastomeric articles have been described above, it should be understood that the present invention is not limited to any particular construction or technique for forming the article. For example, the layers described above may not be utilized in all instances. Additionally, other layers not specifically referred to above may be utilized in the present invention.

The present invention may be better understood with reference to the following examples.

EXAMPLE 1

The ability of a glove of the present invention to permit transpiration of water vapor from the glove's interior during use was demonstrated. Three Safeskin® purple nitrile medium gloves #1–#3 (available from Kimberly-Clark) were provided for testing. These gloves had a palm thickness between 0.08 to 0.16 millimeters and a middle finger thickness of between 0.12 to 0.19 millimeters, as measured at locations specified in ASTM D 3577-99, i.e., for finger thickness, at 13±3 mm from the tip of the glove's middle finger, and for palm thickness, at 33±7 mm from the lowest point between the glove's middle and ring finger and 48±9 mm from the glove's side opposite the thumb. These single thickness measurements were determined using a dial micrometer.

Initially, oval shapes were cut from the top hand side of each glove between the wrist and the knuckles, such as indicated by the area 29 shown in FIG. 1. The cutout area for gloves #1–#3 was 2.6 in$^2$, 2.8 in$^2$, and 5.5 in$^2$, respectively. Thereafter, oval shapes, or patches, of larger size were cut from a breathable film obtained from the fabric used to make MICROCOOL® Surgical Gown, which are available from Kimberly-Clark, Inc. These oval patches had dimensions greater than those cut out from the gloves, i.e., approximately 0.25 to 0.5 inches greater than each glove cut-out portion. The longer dimension of the patch corresponded to the direction that had the least amount of latent extensibility. The film component for the gown fabric was separated from the nonwoven outer facings. The film was made by stretch-thinning a calcium carbonate filled film using known methods, such as described above. The vapor permeability (WVTR) of the film ranged between 4,250 to 8,000 g/m$^2$/24 hours.

The oval patches were then placed over the glove cutouts such that the patches completely covered the glove cutouts and contained the material used to form the breathable zone. Electrical tape strips, used to adhere the patch, overlapped the edge of each patch by 0.33 to 0.5 inches around the entire perimeter and created a hermetic seal between the patch and the rest of the glove.

After forming these gloves, the water vapor transmission rate (WVTR) through each patch was tested as follows. Each glove was first donned on a hand with the glove side having the patch adhered to it contacting the hand (skin).

A pre-weighed strip of a moisture-absorbing film was positioned over each breathable patch. The moisture-absorbing film was made from a poly(ethylene oxide) copolymer (PEO copolymer) that was modified by chemical additives and processing techniques to achieve some amount of crosslinking among the PEO copolymer molecules to allow absorption of, but not dissolution in, water. The PEO copolymer was formed from POLYOX WSR-205 having a molecular weight of 600,000 grams per mole and available from Union Carbide. The chemical additives included 2 mol % of 3-treimthyoxysilyl(propyl) methacrylate, which was available from Dow Corning under the name "Z-6030" as a grafting agent, and a peroxide initiator ("Varox DBPH" available from R. T. Vanderbilt Co., Inc.) in an amount equivalent to 0.33 wt. % of the POLYOX WSR-205. This silane graft-modified PEO resin was thermally processed by extrusion into a film and exposed to ambient conditions to achieve crosslinking.

A small piece of tape was secured to one end of the moisture-absorbing film and to the electrical tape seal to maintain the position of the moisture-absorbing film on top of the patch in the glove's breathable zone. For comparative purposes, a Safeskin® purple nitrile glove containing no breathable zones (no cutouts) was also donned on a hand and had the moisture-absorbing film similarly attached as the glove with the patch. Liquid and vapor impermeable gloves (Safeskin® purple nitrile gloves of larger size) were donned to envelop each of the gloves (those with the breathable patch, the comparative glove with no cut-out portion). Self-adherent wrap having a width of 3 inches (Self-Adherent Wrap, Non-Sterile, Latex-Free, 3 inches×5 yards, available from Kimberly-Clark, Inc.) was wrapped around the open ends of the gloves to compress them around the wrist and confine any moisture vapor transmission through the test gloves within the enveloping gloves. Care was taken to ensure that the time intervals for attaching the moisture-absorbing film and donning the enveloping glove were approximately the same for each test glove (one with the breathable patch, the other the comparative glove with no cut-out portion). After approximately 80 minutes, the enveloping gloves were removed from the corresponding hand.

The moisture-absorbing films were then separated from the gloves and weighed, again ensuring that the time intervals in removing the enveloping gloves, detaching and weighing the moisture-absorbing films were approximately the same. The weight gain for the films was calculated as the weight of the recovered (wet) film, divided by the initial weight of the (dry) film sample minus 1.

The results are set forth below in Table 1:

TABLE 1

Vapor Permeability Results

| Glove | Cutout Area (in$^2$) | Time, minutes | Film Weight Gain (grams) |
|---|---|---|---|
| 1 | 2.6 | 84 | 0.32 |
| 2 | 2.8 | 80 | 0.21 |
| 3 | 5.5 | 78 | 0.94 |
| Comparative | 0 | 78 | 0 |

As indicated above, the gloves #1–#3 each had a weight gain after being worn for approximately 80 minutes. This weight gain was attributed to water vapor transpiring from the hand and through the breathable zone and absorption by the moisture-absorbable film. As noted, the comparative glove was not observed to have any weight gain after being worn for approximately 80 minutes.

In addition, for gloves #1 and #2, approximately 50 milliliters of water were also injected into the gloves while still donned to verify the continued presence of the hermatic seal around the patches. No leakage was visually detected. Thereafter, each glove was removed and completely filled with water. No leakage was observed for the comparative glove and only small leakage spots were observed for gloves #1–#3.

EXAMPLE 2

Various commercially available gloves were compared to a glove formed according to the present invention.

The water vapor transmission rate (WVTR) was initially determined for various commercially available gloves in general accordance with ASTM Standard E-96E-80. Specifically, circular samples measuring three inches in diameter were cut from each of the test materials and a control, which was a piece of CELGARD® 2500 film from Hoechst Celanese Corporation of Sommerville, N.J. CELGARD® 2500 film is a microporous polypropylene film. Three specimens were prepared for each material. The test dishes were number 681 Vapometer cups distributed by Thwing-Albert Instrument Company of Philadelphia, Pa. One hundred milliliters (ml) of distilled water was poured into each Vapometer cup and individual samples of the test materials and control material were placed across the open tops of the individual cups. Screw-on flanges were tightened to form a seal along the edges of each cup (no sealant grease was used), leaving the associated test material or control material exposed to the ambient atmosphere over a 6.5 centimeter (cm) diameter circle having an exposed area of approximately 33.17 square centimeters. The cups were weighed and placed in a forced air oven set at a temperature of 37° C. The oven was a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups were removed from the oven and weighed again. The preliminary test water vapor transmission rate values were calculated as follows:

Test $WVTR$=(grams weight loss over 24 hours)× 315.5 (g/m²/24 hrs)

The relative humidity within the oven was not specifically controlled. Under predetermined set conditions of 37° C. and ambient relative humidity, the WVTR for the CEL-GARD® 2500 film control has been determined to be 5000 grams per square meter for 24 hours (g/m²/24 hrs). Accordingly, the control sample was run with each test and the preliminary test values were corrected to set condition using the following equation:

$WVTR$=(Test $WVTR$/control $WVTR$)×5000 g/m²/24 hrs (g/m²/24 hrs)

The palm thickness was measured for each glove according to the positions specified in ASTM Standard D 3577-99 using a dial micrometer. The palm thickness values were determined by averaging three measurements of both the top and bottom sides together (double layers) of each glove and dividing by 2.

The results are shown below in Table 2.

TABLE 2

WVTR Results for Commercial Gloves

| Sample | Palm Thickness (mm) | WVTR (g/m²/24 hrs) | WVTR Std Dev |
|---|---|---|---|
| Safeskin ® Purple Nitrile ™ | 0.1200 | 142 | 13 |
| Safeskin ® Neon Nitrile ™ | 0.1005 | 178 | 6 |
| Allegiance Flexam ® | 0.1885 | 78 | 7 |
| Safeskin ® Polyvinyl Chloride 52303 ™ | 0.1075 | 135 | 9 |
| Tillotson Ply Nitrile Blend | 0.1035 | 241 | 12 |
| Safeskin ® PFE 440 ™ | 0.1525 | 166 | 62 |
| Safeskin ® Healthtouch ™ | 0.1365 | 105 | 16 |

In addition, a Safeskin® nitrile glove was also formed to include a breathable zone as described in Example 1, (Glove #1). The WVTR and thicknesses for the moisture-impermeable and breathable zones for this glove were also determined. Specifically, the WVTR of the moisture-impermeable zones were determined in general accordance with ASTM Standard E-96E-80, as described above for the moisture-impermeable zone.

However, because ASTM Standard E-96E-80 is bested suited to measure the WVTR of materials only up to about 3000 g/m²/24 hours, the WVTR of materials suitable for use as the breathable zones were determined using a PERMATRAN-W 100K water vapor permeation analysis system, which is commercially available from Modern Controls, Inc. of Minneapolis, Minn. The value for the film obtained from a MICROCOOL®) Surgical Gown was an average of such 32 individual tests. The thickness values for Glove #1 components recorded in Table 3 as Palm Thickness were determined by averaging 3 measurements using a dial micrometer of 2 (double) layers of each type of zone, these double layers formed by folding material in the top and bottom sides of the glove respectively over on itself in the approximate region specified for palm thickness according to ASTM Standard D3577-99, and dividing by 2 to equate them to single layer thickness.

In addition to the WVTR and thickness of Glove #1, values were similarly obtained for two other materials suitable for use as a breathable zone in a glove of the present invention. These two materials were: 1) a nonwoven laminate and 2) a polyurethane film. The nonwoven laminate was made from nonwoven facings and a microporous film used for MICROCOOL® surgical gowns. The polyurethane film was the film component of a SMARTGOWN™ surgical gown sold by Allegiance Healthcare (McGaw Park, Ill. 60085) and was believed to be made from a thermoplastic polyurethane. This film was separated from its attached nonwoven facings.

The results are set forth below in Table 3.

TABLE 3

WVTR Results for Materials Suitable Glove Containing Breathable Zone

| Component | Description | Palm Thickness (mm) | WVTR (g/m²/24 hrs) |
|---|---|---|---|
| Glove #1 (Moisture-impermeable Zone) | Safeskin ® Purple Nitrile ™ | 0.1115 ± 0.0002 | 142 ± 13 |
| Glove #1 (Breathable Zone) | Film from MICROCOOL ® Surgical Gown | 0.0235 ± 0.0010 | 6400 |
| Nonwoven Laminate | Fabric from MICROCOOL ® Surgical Gown | 0.3317 ± 0.0409 | 6400 |
| Polyurethane Film | Film from SMARTGOWN ™ Surgical Gown from Allegiance Healthcare | 0.0153 | 5800–6000 |

As indicated above, the WVTR for the commercially available gloves were generally less than 250 gm/m²/24 hrs. In contrast, the materials suitable for breathable zones provided WVTR values of up to about 6400 g/m²/24 hrs, which would allow water vapor to transpire through the glove during use in addition to possibly escape from the cuff opening.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An elastomeric glove that comprises a substrate body, wherein said substrate body defines at least one breathable zone and at least one moisture-impermeable zone, said moisture-impermeable zone including an elastomeric material, said breathable zone having a water vapor transmission rate that is at least about 15% greater than the water vapor transmission rate of said moisture-impermeable zone, wherein said breathable zone has a moisture vapor transmission rate greater than about 250 grams per square meter per 24 hours, wherein said substrate body forms a palm side, a top hand side, and fingers regions, and wherein said moisture-impermeable zone constitutes at least a portion of said finger regions, said palm side, or combinations thereof.

2. An elastomeric glove as defined in claim 1, wherein said moisture-impermeable zone has a water vapor transmission rate that is less than about 500 grams per square meter per 24 hours.

3. An elastomeric glove as defined in claim 1, wherein said moisture-impermeable zone has a water vapor transmission rate that is less than about 250 grams per square meter per 24 hours.

4. An elastomeric glove as defined in claim 1, wherein said breathable zone has a water vapor transmission rate that is greater than about 1000 grams per square meter per 24 hours.

5. An elastomeric glove as defined in claim 1, wherein said breathable zone has a water vapor transmission rate that is greater than about 3000 grams per square meter per 24 hours.

6. An elastomeric glove as defined in claim 1, wherein said breathable zone has a water vapor transmission rate that is greater than about 5000 grams per square meter per 24 hours.

7. An elastomeric glove as defined in claim 1, wherein said breathable zone has a water vapor transmission rate at least about 50% greater than the water vapor transmission rate of said moisture-impermeable zone.

8. An elastomeric glove as defined in claim 1, wherein said breathable zone has a water vapor transmission rate at least about 100% greater than the water vapor transmission rate of said moisture-impermeable zone.

9. An elastomeric glove as defined in claim 1, wherein said breathable zone constitutes at least a portion of said top hand side.

10. An elastomeric glove as defined in claim 1, wherein said breathable zone contains a breathable film.

11. An elastomeric glove as defined in claim 1, wherein said breathable zone is hermetically sealed to said moisture-impermeable zone.

12. An elastomeric glove as defined in claim 1, wherein said breathable zone is formed from the same material as the moisture-impermeable zone.

13. An elastomeric glove as defined in claim 12, wherein the thickness of said breathable zone is at least about 25% less than the thickness of said moisture-impermeable zone.

14. An elastomeric glove as defined in claim 12, wherein the thickness of said breathable zone is from about 50% to about 95% less than the thickness of said moisture-impermeable zone.

15. An elastomeric glove as defined in claim 1, wherein at least a portion of said substrate body is formed by a dip-forming process.

16. An elastomeric glove as defined in claim 1, wherein the substrate body defines an inside surface, the elastomeric glove further comprising a donning layer that overlies the inside surface of said moisture-impermeable zone.

17. An elastomeric glove as defined in claim 1, further comprising a lubricant that coats the donning layer.

18. An elastomeric glove as defined in claim 1, wherein the thickness of said moisture-impermeable zone is from about 0.01 to about 0.50 millimeters.

19. An elastomeric glove as defined in claim 1, wherein the thickness of said moisture-impermeable zone is from about 0.06 to about 0.35 millimeters.

20. An elastomeric glove as defined in claim 1, wherein the thickness of said breathable zone is from about 0.001 to about 1.5 millimeters.

21. An elastomeric glove as defined in claim 1, wherein the thickness of said breathable zone is from about 0.01 to about 0.03 millimeters.

22. An elastomeric glove that comprises a substrate body, wherein said substrate body defines at least one breathable zone and at least one moisture-impermeable zone, said moisture-impermeable zone including an elastomeric material, said breathable zone having a water vapor transmission rate that is at least about 15% greater than the water vapor transmission rate of said moisture-impermeable zone, wherein said breathable zone has a moisture vapor transmission rate greater than about 250 grams per square meter per 24 hours, wherein said breathable zone contains at least one material that is different than the material forming said moisture-impermeable zone.

23. An elastomeric glove that comprises a substrate body, wherein said substrate body defines at least one breathable zone and at least one moisture-impermeable zone, said moisture-impermeable zone including an elastomeric material, said breathable zone having a water vapor transmission rate that is at least about 15% greater than the water vapor transmission rate of said moisture-impermeable zone, wherein said breathable zone has a moisture vapor transmission rate greater than about 250 grams per square meter per 24 hours, wherein said breathable zone is formed from the same material as the moisture-impermeable zone, wherein said elastomeric material is polyurethane.

24. An elastomeric glove that comprises a substrate body, wherein said substrate body defines at least one breathable zone and at least one moisture-impermeable zone, said moisture-impermeable zone including an elastomeric material, said breathable zone having a water vapor transmission rate that is at least about 100% greater than the water vapor transmission rate of said moisture-impermeable zone, wherein said breathable zone has a moisture vapor transmission rate greater than about 3000 grams per square meter per 24 hours, wherein said substrate body forms a palm side, a top hand side, and fingers regions, and wherein said moisture-impermeable zone constitutes at least a portion of said finger regions, said palm side, or combinations thereof.

25. An elastomeric glove as defined in claim 24, wherein said moisture-impermeable zone has a water vapor transmission rate that is less than about 500 grams per square meter per 24 hours.

26. An elastomeric glove as defined in claim 24, wherein said moisture-impermeable zone has a water vapor transmission rate that is less than about 250 grams per square meter per 24 hours.

27. An elastomeric glove as defined in claim 24, wherein said breathable zone has a water vapor transmission rate that is greater than about 5000 grams per square meter per 24 hours.

28. An elastomeric glove as defined in claim 24, wherein said breathable zone contains at least one material that is different than the material forming said moisture-impermeable zone.

29. An elastomeric glove as defined in claim 24, wherein said breathable zone is formed from the same material as the moisture-impermeable zone.

30. An elastomeric glove as defined in claim 29, wherein said elastomeric material is polyurethane.

31. An elastomeric glove as defined in claim 29, wherein the thickness of said breathable zone is from about 50% to about 95% less than the thickness of said moisture-impermeable zone.

32. An elastomeric glove as defined in claim 24, wherein at least a portion of said substrate body is formed by a dip-forming process.

33. An elastomeric glove that comprises a substrate body that forms a palm side, a top hand side, and fingers regions, wherein at least a portion of said top hand side is constituted by a breathable zone and at least a portion of said finger regions, said palm side, or combinations thereof, is constituted by a moisture-impermeable zone, wherein said breathable zone has a moisture vapor transmission rate greater than about 3000 grams per square meter per 24 hours and said moisture-impermeable zone has a water vapor transmission rate that is less than about 250 grams per square meter per 24 hours.

34. An elastomeric glove as defined in claim 33, wherein said breathable zone has a water vapor transmission rate that is greater than about 5000 grams per square meter per 24 hours.

35. An elastomeric glove as defined in claim 33, wherein at least a portion of said substrate body is formed by a dip-forming process.

* * * * *